United States Patent [19]
Alderson et al.

[11] 4,424,234
[45] Jan. 3, 1984

[54] SKIN TREATMENT COMPOSITIONS

[75] Inventors: Susan G. Alderson, Morecambe; Martin D. Barratt, Sharnbrook; John G. Black, Harrold, all of England

[73] Assignee: Lever Brothers Company, New York, N.Y.

[21] Appl. No.: 220,875

[22] Filed: Dec. 29, 1980

Related U.S. Application Data

[63] Continuation-in-part of Ser. No. 203,287, Nov. 3, 1980, abandoned, which is a continuation of Ser. No. 59,912, Jul. 23, 1979, abandoned.

[30] Foreign Application Priority Data

Jul. 24, 1978 [GB] United Kingdom ............... 30871/78

[51] Int. Cl.³ ...................... A61K 31/19; A61K 31/20

[52] U.S. Cl. .................................. 424/317; 424/318; 424/DIG. 5; 424/45

[58] Field of Search ................ 424/317, 318; 260/413; 562/512

[56] References Cited

U.S. PATENT DOCUMENTS

| | | | |
|---|---|---|---|
| 3,320,230 | 5/1967 | Bennett ........................... | 562/512 X |
| 3,879,537 | 4/1975 | Van Scott et al. .................. | 424/311 |
| 4,105,783 | 8/1978 | Yu et al. ............................ | 424/283 |

*Primary Examiner*—Leonard Schenkman
*Attorney, Agent, or Firm*—Amirali Y. Haidri; James J. Farrell

[57] ABSTRACT

A cosmetically acceptable aqueous composition for topical application to human skin to provide skin benefit comprises an hydroxylated $C_6$ to $C_{10}$ carboxylic acid and a cosmetically acceptable vehicle other than water.

5 Claims, No Drawings

SKIN TREATMENT COMPOSITIONS

This application is a continuation-in-part application of application Ser. No. 203,287 filed Nov. 3, 1980 now abandoned, which is a continuation application of application Ser. No. 059,912 filed July 23, 1979 now abandoned.

The invention relates to aqueous skin treatment compositions and in particular to compositions which reduce the dryness of flakiness of skin and which can improve the suppleness or smoothness of skin.

A soft, supple and flexible skin has a marked cosmetic appeal and is an attribute of normal functioning epidermis. The outer layer of the epidermis, i.e. the stratum corneum, can, however, become dry and flaky following exposure to adverse climatic conditions, or excessive contact with detergents or solvents which result in loss of skin moisture, with the result that the skin loses its soft, supple and flexible characteristics. Emollients such as fats, phospholipids and sterols have in the past been used to soften dry skin, but it is apparent that these emollients are only partially effective as a remedy for this type of condition.

Also, topical application to the skin of classical humectants is unlikely to alleviate this problem since they are not particularly skin substantive and are generally rinsed from the skin during washing.

It is therefore evident that there exists a need for an effective treatment for skin which is in a dry, flaky condition and which is relatively inflexible.

As part of a program to examine substances for their ability to improve skin condition, isolated guinea pig footpad stratum corneum was selected as a test substrate and changes in its extensibility were measured after application of each test substance. The amount by which extensibility was increased was taken as a measure of the likely skin benefit that the substance might have on human skin. The isolated guinea pig footpad stratum corneum was usually first 'damaged' by immersion in diethyl ether so that any benefit derived from subsequent treatment with a test substance could more readily be recognised. Of the many substances screened in this way, it was discovered that, at low concentrations, certain hydroxylated carboxylic acids of medium chain length were effective in increasing the extensibility of solvent damaged guinea pig footpad stratum corneum while short and long chain hydroxylated carboxylic acids did not achieve this effect.

Following this initial discovery, it was subsequently confirmed by subjective assessment that the condition of human skin, particularly that which is in a dry, flaky and relatively inflexible condition, can be improved by topical application of such substances.

Accordingly, the invention provides a cosmetically acceptable aqueous composition for topical application comprising a skin benefit inducing amount of an hydroxylated carboxylic acid having from 6 to 10 carbon atoms in the molecule, together with a cosmetically acceptable vehicle other than water.

THE HYDROXYLATED CARBOXYLIC ACID

The likelihood of an hydroxylated carboxylic acid being capable of improving the condition of skin to which it is applied can first be assessed objectively by an in vitro method which involves measuring the change in extensibility of isolated stratum corneum to which the acid is applied. The technique employed will be described in detail later in the specification. A significant increase in extensibility can then be taken as an indicator that the acid, when applied to living human skin, is likely to improve the condition of that skin in terms of softness, suppleness and flexibility. Confirmation of this can be obtained by clinical studies which will also be described later.

Based on the results of these in vitro studies with isolated stratum corneum, it has been shown that the hydroxylated carboxylic acids for use in compositions according to the invention should have from 6 to 10 carbon atoms in the molecule, have one or more hydroxyl groups, are straight or branched chained and can be saturated or unsaturated.

Preferably, the carboxylic acid is a saturated acid with a single hydroxyl group in the α-position. Examples are α-hydroxy-iso-caproic acid, α-hydroxy-n-caproic acid, α-hydroxy-iso-caprylic acid, α-hydroxy-n-caprylic acid and α-hydroxy-n-capric acid.

Of these, the acid which produces the greatest increase in extensibility of the stratum corneum is α-hydroxy-n-caprylic acid.

Comparative measurements have shown that hydroxylated carboxylic acids having less than 6 carbon atoms or conversely more than 10 carbon atoms in the molecule, exhibit little or no increase in extensibility of stratum corneum when tested by the in vitro method to be described hereinafter.

It is furthermore apparent that the maximum benefit is obtained when the hydroxylated carboxylic acid is employed as the free acid rather than as a corresponding salt or ester. The pH value of the composition is accordingly less than 7 and is usually from 2 to 4.

The amount of hydroxylated carboxylic acid employed is from 0.5 to 20%, preferably from 1 to 10% by weight of the composition. Expressed in terms of molar concentrations this is approximately equivalent to 0.01 M to 1 M, preferably 0.05 M to 0.5 M.

It should be explained that use of less than 0.5% of the hydroxylated carboxylic acid by weight of the composition is unlikely to confer on the user any noticeable skin benefit. The upper limits, on the other hand, are dictated more by the nature of the composition, i.e. solid or liquid, than by any limit of efficacy of the hydroxylated carboxylic acid as a skin benefit agent.

WATER

The composition also comprises water. The quantity of water in the composition is from 1 to 99.4%, preferably from 10 to 90% by weight of the composition.

COSMETICALLY ACCEPTABLE VEHICLE OTHER THAN WATER

The selection of a vehicle other than water for hydroxylated carboxylic acids in the compositions of the invention presents a wide range of possibilities depending on the required product form of the composition. Suitable vehicles can be classified as described hereinafter.

It should be explained that vehicles are substances which can act as diluents, dispersants, or carriers for the hydroxylated carboxylic acids and which therefore ensure that they can be applied to and distributed evenly over the skin at an appropriate concentration; in certain cases, the vehicle can aid its penetration into the stratum corneum, thus ensuring that the effectiveness of the applied hydroxylated carboxylic acids are prolonged because of improved substantivity. Clearly water which is present in compositions of the invention can act in this way as a vehicle, but it is to be understood that these compositions should contain at least one other vehicle in addition to water.

The vehicles other than water that can be used in compositions according to the invention can include solid, especially powdered vehicles such as moisture absorbents, powdered binders and diluents and liquids such as emollients, propellants, solvents, humectants and thickeners. Examples of each of these types of vehicles, which can be used singly or as mixtures of one or more vehicles, are as follows:

MOISTURE ABSORBENTS

Carragheenates
Pectins
Polyvinyl alcohol
Polyethylene oxides
Polyvinylpyrrolidone
Carboxyvinyl polymers
Copolymers of methyl vinyl ether
Maleic anhydrides
Mixed salts of calcium and sodium alginate
Crosslinked dextrans
Chemically modified cellulose
Microcrystalline cellulose
Calcium alginate
Alginic acid
Pregelatinised starches
Chemically modified starches
Crosslinked starches
Starch copolymers such as hydrolysed (particularly base-hydrolysed) starch
Polyacrylonitrile graft copolymers
Crosslinked polyacrylamides
Crosslinked polyacrylic acids
Crosslinked polyhydroxyethyl methacrylate
Crosslinked polyvinyl alcohol
Crosslinked polyvinylpyrrolidone
Sulphonated polystyrene crosslinked with di-vinylbenzene
Quaternised polyvinyl pyridine crosslinked with divinyl benzene
Magnesium silicate
Lanolin absorption base
Amorphous silica powder

POWDER BINDERS AND DILUENTS

Microcrystalline cellulose
Isostearyl neopentanoate
Polyacrylamide
Lauryl lactate
Precipitated silica
Talc
Chalk

EMOLLIENTS

Stearyl alcohol
Glyceryl monoricinoleate
Glyceryl monostearate
Sulphated tallow
Propylene glycol
Mink oil
Cetyl alcohol
Stearyl stearate
Isopropyl isostearate
Dimethyl brassylate
Stearic acid
Isobutyl palmitate
Isocetyl stearate
Oleyl alcohol
Isopropyl laurate
Hexyl laurate
Decyl oleate
Di-isopropyl adipate
2-octadecanol
Iso-cetyl alcohol
Myristyl ethoxymyristate
Cetyl palmitate
Dimethylpolysiloxane
Di-isopropyl adipate
Di-n-butyl sebacate
Di-isopropyl sebacate
Di-2-ethyl hexyl sebacate
2-ethyl hexyl palmitate
Isononyl isononanoate
Isodecyl isononanoate
Isotridecyl isononanoate
2-ethyl hexyl palmitate
2-ethyl hexyl stearate
Di-(2-ethyl hexyl) adipate
Di-(2-ethyl hexyl) succinate
Isopropyl myristate
Isopropyl palmitate
Isopropyl stearate
Butyl stearate
Glyceryl monostearate
Polyethylene glycol
Propylene glycol
Triethylene glycol
Lanolin
Castor oil
Acetylated lanolin alcohols
Acetylated lanolin
Petrolatum
Isopropyl ester of lanolin fatty acids
Mineral oils
Butyl myristate
Isostearic acid
Palmitic acid
Isopropyl linoleate
Cetyl lactate
Lauryl lactate
Myristyl lactate
Quaternised hydroxy alkyl aminogluconate
Decyl oleate
Isodecyl oleate
Di-isopropyl adipate
2-ethyl hexyl palmitate
Isostearyl neopentanoate
Myristyl myristate
Di-isopropyl adipate
Oleyl ethoxy myristate
Diglycol stearate
Ethylene glycol monostearate
Myristyl stearate
Isopropyl lanolate

PROPELLANTS

Trichlorofluoromethane
Dichlorodifluoromethane
Dichlorotetrafluoroethane
Monochlorodifluoromethane
Trichlorofluoroethane
Propane
Butane Isobutane
Dimethyl ether
Carbon dioxide

SOLVENTS

Ethyl alcohol
2-ethyl hexanol
Ethylene carbonate
Propylene carbonate
Methylene chloride
Isopropyl alcohol
Castor oil
Linear ethoxylated polymer of methanol
Ethylene glycol monoethyl ether
Diethylene glycol monobutyl ether
Diethylene glycol monoethyl ether
Propoxylated butanol
Propoxylated oleyl alcohol
Butyl stearate
Butyl myristate

HUMECTANTS

Glycerin
Sorbitol
Sodium 2-pyrrolidone-5-carboxylate
Soluble collagen
Dibutyl phthalate
Gelatin
Polyglycerogen
Ethoxylated (10–20 moles) glucose
Propoxylated (10–20 moles) glucose

THICKENERS AND STABILISERS

Gums
Starch
Colloidal silicon dioxide
Sodium polyacrylate
Tetra alkyl and/or trialkyl aryl ammonium smectites
Chemically modified magnesium aluminium silicate
Organically modified montmorillonite clay
Hydrated aluminium silicate
Fumed silica
Carboxyvinyl polymer
Sodium carboxymethyl cellulose
Hydroxyethyl stearate amide
Ethylene glycol monostearate The quantity of vehicle other than water employed can constitute the balance of the product, or a smaller proportion than the balance, provided that it is capable of performing its function as herein defined.

The vehicle other than water will accordingly comprise from 0.1 to 98.5, preferably from 5 to 80% by weight of the composition.

The composition according to the invention can contain ingredients other than those already mentioned, depending on the form of the intended product. It is, for example, possible to include moisturisers, sunscreen agents, antiseptics or preservatives, antioxidants, anti-caking agents, emulsifiers, perfumes and colouring agents. Examples of some of the ingredients are as follows:

MOISTURISERS

Sodium pyrollidone carboxylate
Sodium lactate
Orotic acid

SUNSCREEN AGENTS p-aminobenzoic acid
Ethylene glycol salicylate
Propoxylated (2 moles) ethyl p-aminobenzoate
Dipropylene glycol salicylate
2-ethoxyethyl-p-methoxy cinnamate
Cetyl stearyl alcohol
2-hydroxy-4-methoxybenzophenone-5-sulphonic acid
Ethylhexyl-2-cyano-3,3-diphenyl acrylate
Urocanic acid
2-hydroxy-4-octyloxybenzophenone
Methyl-p-hydroxybenzoate
Homomenthyl salicylate

ANTISEPTICS AND PRESERVATIVES 2-bromo-2-nitro propan-1,3-diol
Cetyl pyridinium chloride
3,4,4'-trichlorocarbanilide
2,4,4'-trichloro-2'-hydroxydiphenyl ether
Benzalkonium chloride
Para hydroxy benzoic acid
Dehydroacetic acid
Formaldehyde
EDTA

ANTIOXIDANTS

Tocopherol
Ascorbyl palmitate
Propyl gallate
Butylated hydroxy toluene
Butylated hydroxyanisole

ANTI-CAKING AGENTS

Hydrophobic starch
Silicone dioxide

ANIONIC EMULSIFIERS

Potassium stearate
Sodium stearate
Ammonium stearate
Triethanolamine stearate
Glyceryl monostearate containing either potassium or sodium soap
Sodium lauryl sulphate
Sodium cetyl sulphate
Glyceryl monostearate containing sodium lauryl sulphate

CATIONIC EMULSIFIERS

N(stearoyl colamino formylmethyl) pyridinium chloride
N-soya-N-ethyl morpholinium ethosulphate
Alkyl dimethyl benzyl ammonium chloride
Di-isobutylphenoxyethoxyethyl dimethyl benzyl ammonium chloride
Cetyl pyridinium chloride

NONIONIC EMULSIFIERS

Fatty acid esters of sorbitan anhydrides or ethylene oxide products of sorbitan fatty acid esters such as Span 80 or Tween 80; and pluronics which are addition products of hydrophilic polyoxy ethylene groups and a hydrophilic polyoxy propylene.

The amount of emulsifiers, if used, usually form from 1 to 10%, preferably 1 to 5% by weight of the composition.

The benefit to the skin derived from topical application of the composition can be assessed objectively by measuring the increase in extensibility of isolated stratum corneum following application of the composition to damaged stratum corneum.

MEASURING THE EXTENSIBILITY OF ISOLATED STRATUM CORNEUM

Stratum corneum is obtained from the rear feet of guinea pigs and prepared in a similar manner to that described by Middleton (1968) in Brit.J.Dermatol.80, 437. The dissected footpads are incubated for 18 hours at 37° C. in a solution of 0.5% (w/v) Trypsin (Koch-Light, ex Hog pancreas) and 2 M urea dissolved in 0.1 M tris (pH 7.4 HCl) and 0.02% (w/v) sodium azide. After digestion, the underlying tissues of dermis and lower layers of epidermis are scraped away and the remaining transparent stratum corneum is washed twice in cold distilled water for two periods of two hours.

The samples of stratum corneum are kept in pairs throughout the experiment so that one of each pair acts as a control.

Solvent damaged stratum corneum is prepared by immersing paired samples of stratum corneum in 10 ml diethyl ether (AR grade) at 25° C. for 18 hours. After this treatment, the samples are washed in excess cold distilled water to remove loosened fragments of stratum corneum cells adhering to the surface, and then immersed in 10 ml of cold distilled water for 15 hours with 3 changes of water to remove hygroscopic substances within the stratum corneum cells responsible for water binding.

Undamaged or solvent damaged samples of stratum corneum are thoroughly dried with filter paper after immersing in water and cut into rectangular strips 1.5×0.5 cm with a stainless steel punch. Control samples are washed in 10 ml of cold distilled water at room temperature while the corresponding strips from the other footpads are immersed in 2 ml of the treatment solution under investigation. After 18 hours the pairs of stratum corneum are removed, dried with filter paper, transferred into labelled vials and placed in a humidifier at 81% relative humidity using a saturated solution of potassium bromide. The stratum corneum samples are left to equilibrate at 81% RH for 10 days.

The extensibility of guinea pig stratum corneum is measured on an Instron Tester as described by Middleton (Supra). Pneumatic jaws, one serrated and one rubber pad, operate at a pressure of 15–20 psi inside a double walled perspex cabinet, in which air, circulated by a fan, is recycled through a saturated solution of potassium bromide. A wet and dry bulb hygrometer, positioned inside the cabinet, measures the enclosed humidity. Stratum corneum samples are handled with rubber gloves through ports in the cabinet. The lower jaw assembly and humidity cabinet remains fixed to the crosshead, whilst the upper jaw assembly connected to a 2 kg load cell type B mounted on top of the crosshead, rises at a speed of 0.5 cms $min^{-1}$. The jaws are separated by a distance of 0.5 cm and the corneum strips are positioned between them. The extension cell is subjected to an increasing load as the strips are extended. This is recorded on a monitor, set at full scale deflection of 1 kg force and a speed of 20 cms $min^{-1}$.

The extensibility of the stratum corneum strips is expressed as % extension/100 g load, if necessary allowing for slack.

Individual experiments are performed on 20 samples of paired footpads. The sample mean is calculated for each set and mean differences between control and test extensibilities are analysed statistically by student t-tests to obtain significance levels.

EXPERIMENT

Extensibility measurements on undamaged and solvent damaged stratum corneum were carried out following treatment with solutions of α-hydroxy carboxylic acids according to the method described hereinbefore. The solutions employed were 0.15 M aqueous solutions of the α-hydroxy acids at a pH value of from 2 to 3. The results obtained when using undamaged isolated stratum corneum showed that treatment with α-hydroxy-n caproic acid and with α-hydroxy-n caprylic acid induced a significant increase in extensibility. The results obtained when using solvent damaged stratum corneum also indicated that a significant increase in extensibility was obtained following treatment with these acids. These latter results together with those obtained following treatment with other α-hydroxy carboxylic acids are summarised in Table 1 below.

TABLE 1

Extensibilities of solvent-damaged guinea pig footpads before and after treatment with various α-hydroxy carboxylic acids

| 0.15M aqueous solution of acid | pH | % extensibility/100 g | | | Standard Deviation | Significance of difference (for 20 replicates) |
|---|---|---|---|---|---|---|
| | | Control | Treated | Difference | | |
| lactic acid ($C_3$) | 2.33 | 1.40 | 1.75 | 0.35 | 1.00 | NS* |
| α-hydroxy-n-butyric ($C_4$) | 2.20 | 1.76 | 2.32 | 0.56 | 1.26 | NS* |
| α-hydroxy-n-caproic ($C_6$) | 2.12 | 1.97 | 4.94 | 2.97 | 3.37 | >99.9% |
| α-hydroxy-n-caprylic ($C_8$) | 2.40 | 1.64 | 8.42 | 6.78 | 3.37 | >99.9% |
| α-hydroxy-n-capric ($C_{10}$) | 3.19 | 1.00 | 2.44 | 1.44 | 2.18 | >98% |

NS*: not significant at 95% level

Saturated solutions of α-hydroxy lauric acid ($C_{12}$) and of α-hydroxy myristic acid ($C_{14}$), both of which had a pH of 7, were also tested in the same way using solvent damaged stratum corneum: there was however no significant difference in extensibility demonstrated between control and treated footpads for each of these acids, probably because of their low solubility in water.

Otherwise, the tabulated results show a superiority for α-hydroxy-n-caproic acid ($C_6$) and α-hydroxy-n-caprylic acid ($C_8$) as compared with an insignificant effect after treatment with both lactic acid ($C_3$) and α-hydroxy-n-butyric acid ($C_4$) and a barely demonstrable effect after treatment with α-hydroxy-n-capric acid ($C_{10}$).

PRODUCT FORMS

The compositions of the invention can be formulated as liquid, for example products such as lotions for use in conjunction with applicators such as a roll-ball applicator or a spray device such as an aerosol can containing propellant or a container fitted with a pump to dispense the product. Alternatively, the compositions of the invention can be solid or semi-solid, for example moulded sticks, creams or gels, for use in conjunction with an applicator such as a stick applicator, or simply a tube or lidded jar.

The invention accordingly also provides a closed container containing a cosmetically acceptable composition as herein defined.

The invention further provides a process for preparing a cosmetically acceptable aqueous composition for topical application to human skin, which process comprises mixing an hydroxylated carboxylic acid having from 6 to 10 carbon atoms in the molecule, with a cosmetically acceptable vehicle other than water.

Compositions according to the invention are intended for topical application to human skin which is already in a dry, flaky or relatively inflexible condition or prophylactically to normal healthy skin to prevent or reduce deteriorative changes of this sort.

The compositions are of particular benefit if applied to exposed skin areas during cold weather, or during exposure to strong sunlight sufficient to cause sunburn, or when the skin is exposed to repeated contact with detergents or solvents. In each of these situations, the drying and tightening of the skin with subsequent breakdown to give flaking, peeling or cracking can be reduced or prevented with topical application to affected skin areas of compositions according to the invention.

The invention is illustrated by the following Examples of cosmetically acceptable compositions for topical application to human skin.

EXAMPLE 1

This example illustrates an aerosol lotion which can be prepared from the following ingredients.

| | % w/w |
|---|---|
| Polyethylene glycol 1000 monostearate | 2.4 |
| Lanolin alcohols | 1.0 |
| Linear alcohol lactate | 2.0 |
| Myristyl myristate | 1.5 |
| Mineral oil 65/75 | 3.8 |
| $\alpha$-hydroxy-n-caprylic acid ($C_8$) | 2.0 |
| Cationic detergent | 1.0 |
| Water | 62.3 |
| Alcohol | 12.0 |
| Propellant 12/114 (Dichlorodifluoromethane: dichlorofluoroethane - 40:60) | 12.0 |

EXAMPLE 2

This example illustrates a face cream which can be prepared from the following ingredients, the oil phase and the aqueous phase being subsequently emulsified.

| | % w/w |
|---|---|
| (i) Oil phase | |
| Stearic acid | 18.0 |
| Mineral oil | 5.0 |
| Polyoxyethylene (20) propylene glycol monostearate | 5.0 |
| Propyl-p-hydroxy benzoate | 0.05 |
| (ii) Aqueous phase | |
| Propylene glycol | 5.0 |
| 2-pyrollidone-5-carboxylic acid | 5.0 |
| Sodium hydroxide | 1.6 |
| $\alpha$-hydroxy-n-caprylic acid ($C_8$) | 2.0 |
| Triethanolamine | 1.0 |
| Methyl-p-hydroxy benzoate | 0.1 |
| Water | 57.25 |

EXAMPLE 3

This example illustrates a sunscreen cream which can be prepared by blending the following ingredients:

| | % w/w |
|---|---|
| Stearic acid | 2 |
| Wool alcohol | 1 |
| Cetyl alcohol | 3.5 |
| Polar wax, a polyoxyethylene ester of sorbitan | 5 |
| Arachis oil | 15 |
| Ethyl-p-dimethylaminobenzoate | 0.75 |
| Ethyl-p-diethylaminobenzene | 0.75 |
| Butylated hydroxy toluene | 0.02 |
| Glycerin | 3 |
| Sodium citrate | 0.05 |
| Methyl-p-hydroxybenzoate | 0.1 |
| Silicon fluid MS200 | 1 |
| Perfume oil | 0.4 (v/w) |
| $\alpha$-hydroxy caproic acid ($C_6$) | 8 |
| Water | 59.43 |

EXAMPLE 4

This example illustrates a handcream which can be prepared by blending the following ingredients:

| | % w/w |
|---|---|
| Isopropyl myristate | 3.0 |
| Polyethylene glycol (1000) monostearate | 5.0 |
| Stearic acid | 19.0 |
| Methyl paraben | 0.15 |
| Polyethylene glycol (300) monostearate | 5.0 |
| Sorbitol | 3.0 |
| $\alpha$-hydroxy iso-caprylic acid ($C_8$) | 1.0 |
| Water | 63.85 |
| Perfume and colour | q.s. |

EXAMPLE 5

This example illustrates an all-purpose mask which can be prepared by blending the following ingredients:

| | % w/w |
|---|---|
| Kaolin | 35.0 |
| Bentonite | 5.0 |
| Cetyl alcohol | 2.0 |
| Sodium lauryl sulphate | 1.0 |
| Glycerin | 10.0 |
| Nipagin M | 0.1 |
| $\alpha$-hydroxy-n-caprylic acid ($C_8$) | 5.0 |
| Perfume | q.s. |
| Water | 41.9 |

EXAMPLE 6

This example illustrates a toothpaste which can be prepared from the following ingredients:

| | % w/w |
|---|---|
| $\alpha$-hydroxy-n-caproic acid ($C_6$) | 3.0 |
| Aluminium hydroxide (microcrystalline) | 41.5 |

| | % w/w |
|---|---|
| Alumina (aluminium oxide) | 2.0 |
| Glycerol | 28.0 |
| Water | 24.5 |
| Sodium lauryl sulpho acetate | 1.0 |
| Flavour | 0.7 |
| Gum tragacanth | 0.5 |
| Methyl-p-hydroxybenzoate | 0.1 |
| Saccharin | 0.05 |
| Phosphoric acid to produce a pH of 6.5 to 7.5 | q.s. |

EXAMPLE 7

This example illustrates a skin milk which can be prepared from the following ingredients:

| | % w/w |
|---|---|
| Glyceryl monomyristate | 3 |
| Isopropyl isostearate | 8 |
| Oil | 3 |
| α-hydroxy iso-caproic ($C_6$) | 2 |
| Carbopol 941 | 0.2 |
| TEA | 0.15 |
| Water | 83.65 |

EXAMPLE 8

This example illustrates a cream containing α-hydroxy caproic acid and its effect when applied to the human face during the winter months when exposure to cold weather was anticipated.

For the purposes of the human test, two creams were prepared—a test cream containing α-hydroxy-n caproic acid and a control cream containing no acid (cream base).

The cream base had the following formulation.

| | % w/w |
|---|---|
| MYRJ 52 (polyoxyethylene 40-stearate) | 1.0 |
| CUTINA MD (ethylene glycol mono- and di-glyceride) | 5.0 |
| LANOL 14M (myristyl ethoxy myristate) | 0.5 |
| ALFOL 18RD (synthetic $C_{18}$ alcohol) | 1.0 |
| CUTINA CP (cetyl palmitate) | 2.5 |
| NIPANOL M (propyl p-hydroxybenzoate) | 0.1 |
| NIPAGEN M (ethyl p-hydroxybenzoate) | 0.2 |
| Glycerol | 3.0 |
| RHODAPOL (heteropolysaccharides) | 0.1 |
| Water | 86.6 |

α-hydroxy-n-caproic acid, 4.0% w/w, was added to the cream base formulation and the pH adjusted to 3.5 by addition of sodium hydroxide to provide the test cream.

A panel of 54 female subjects was recruited for the test and each panellist was provided with both test and control creams. 0.2 g of each cream was applied to each half face area twice daily under laboratory conditions and a tube of each cream was provided for similar use outside the laboratory. Faces were assessed in the laboratory by expert assessors for dryness and flakiness at the commencement of the test and twice a week for up to 4 weeks. 49 panellists completed the trial.

Data for the whole trial period were examined using analysis of variance. A two-way product and subject analysis was carried out and the mean change in half-face score using the initial half-face score as co-variable was calculated.

The results indicated that the test cream induced a statistically significant improvement (>90% level) in the condition of the skin of the lower cheek during the test period.

EXAMPLE 9

This example illustrates a cream containing α-hydroxy caproic acid and its effect when applied to the human hand, again during the winter months when exposure to cold weather was most likely to exacerbate skin problems.

For the purposes of the hand test, the test and control creams described in Example 8 were employed, except that they were unbuffered and had a pH of about 2.5.

A panel of 13 male and 37 female subjects was recruited for the test and each panellist was provided with both test and control creams.

Cream was applied to the backs of each hand, particularly to the finger webs, at least twice daily over a period of six weeks. The hands of the panel were assessed for skin dryness once a week during the clinical trial by expert assessors.

Statistical analysis of the accumulated data showed that at certain stages during the trial following exposure to particularly cold weather, the skin of the finger and thumb webs of the hand receiving the test cream were significantly less dry than the webs of the hand receiving the control cream, thus indicating that the α-hydroxy caproic acid had a benefitting effect on the skin. Improvements to the skin of hands receiving the test cream during periods of milder weather were not so marked.

It was, however, concluded from the results of both of the clinical trials described in Examples 8 and 9 that there was sufficient correlation between in vitro and in vivo (clinical) studies to predict from isolated stratum corneum extensibility data, the likelihood of skin benefit to the human subject following topical application of compositions of the invention.

Evidence for this latter conclusion can, for example, be derived from an examination of the in vitro data obtained when the test and conrol creams described in Example 8 were applied to isolated stratum corneum and the extensibility measured as hereinbefore described.

The data obtained are summarised in Table 2 below.

TABLE 2

| The effect of α-hydroxy-n-caproic acid in a cream base* on the extensibility of normal and solvent damaged guinea pig footpad stratum corneum ||||||| 
|---|---|---|---|---|---|
| Substrate | pH | Control (c) | Test (t) | Difference | Standard Deviation of Difference | Significance level (20 replicates) |
| (a) Normal stratum corneum | | | | | | |
| c = base cream | 2.2 | 3.32 | 23.19 | 19.87 | 16.72 | >99% |
| t = base cream + | 3.5 | 1.82 | 2.79 | 0.97 | 1.16 | >99% |

TABLE 2-continued
The effect of α-hydroxy-n-caproic acid in a cream base* on the extensibility of normal and solvent damaged guinea pig footpad stratum corneum

| Substrate | pH | Control (c) | Test (t) | Difference | Standard Deviation of Difference | Significance level (20 replicates) |
|---|---|---|---|---|---|---|
| 0.3M acid | | | | | | |
| (b) Solvent damaged stratum corneum | | | | | | |
| c = base cream | 2.2 | 2.55 | 15.49 | 12.96 | 7.32 | >99.9% |
| t = base cream + 0.3M acid | 3.5 | 1.77 | 3.17 | 1.40 | 1.25 | >99% |
| c = water | 7.0 | 0.93 | 1.18 | 0.25 | 1.04 | Not significant |
| t = base cream | | | | | | |

*as described in Example 11 with or without adjustment of pH.

It will be noted from this Table of results that the extensibility of isolated stratum corneum was significantly increased following treatment with a cream containing α-hydroxy-n-caproic acid, compared with that following application of a control base cream which contained none of the acid. The significance of the increase was more dramatic with solvent damaged stratum corneum as the substrate, than with normal stratum corneum. A comparison of isolated solvent damaged stratum corneum treated with water versus cream base showed no significant increase in extensibility due to the cream base itself.

These in vitro results correlated well with the results of the corresponding in vivo tests using human subjects described in Examples 8 and 9.

What is claimed is:

1. A cosmetically acceptable aqueous composition in the form of lotions, creams, gels and solid sticks for topical application to the skin, comprising from 0.5 to 20% by weight of an hydroxy alkanoic acid selected from the group consisting of α-hydroxy-n-caproic acid, α-hydroxy-n-caprylic acid and mixtures thereof, together with a cosmetically acceptable vehicle other than water.

2. The composition according to claim 1, wherein the hydroxy alkanoic acid forms from 1 to 10% by weight of the composition.

3. The composition according to claim 1, wherein the vehicle is selected from the group consisting of powder absorbents, powder binders, powder carriers, emollients, propellants, solvents, humectants, thickeners and mixtures thereof.

4. The composition according to claim 3, wherein the vehicle comprises up to 99.5% by weight of the composition.

5. A method of treating dry skin which comprises applying to said dry skin an effective amount to reduce dryness of a composition according to claim 1.

* * * * *